United States Patent [19]

Opara

[11] Patent Number: 4,470,306

[45] Date of Patent: Sep. 11, 1984

[54] ULTRASONIC TEST INSTRUMENT

[75] Inventor: Ulrich Opara, Erfstadt-Köttingen, Fed. Rep. of Germany

[73] Assignee: Krautkramer-Branson, Inc., Lewistown, Pa.

[21] Appl. No.: 479,443

[22] Filed: Mar. 28, 1983

[30] Foreign Application Priority Data

May 15, 1982 [DE] Fed. Rep. of Germany ....... 3218440

[51] Int. Cl.³ .......................................... G01N 29/04
[52] U.S. Cl. .................................... 73/627; 73/602; 73/632
[58] Field of Search ................. 73/629, 627, 602, 618, 73/620, 632, 641

[56] References Cited

U.S. PATENT DOCUMENTS

| 3,453,871 | 7/1969 | Krautkramer | 73/629 |
| 4,016,750 | 4/1977 | Green | 73/629 |
| 4,197,750 | 4/1980 | Hassler | 73/629 |
| 4,277,978 | 7/1981 | Puckette | 73/632 |

Primary Examiner—Stephen A. Kreitman
Attorney, Agent, or Firm—Ervin B. Steinberg; Philip J. Feig

[57] ABSTRACT

This invention relates to ultrasonic test instruments using wide-band test probes of different nominal frequencies fo and discloses an arrangement wherein each wide-band test probe of different nominal frequency fo is coupled in circuit with a receiving amplifier having a frequency response V(f). The frequency response of the receiving amplifier is so selected that the product H(f) comprising the spectral distribution S(f) of the transmitter and the frequency response V(f) of the receiving amplifier is substantially constant approximately up the the nominal frequency fo of the test probe and has its maximum value in that range. For the transmitters conventionally used in ultrasonic test instruments, in which the transmission pulse is generated by a capacitor discharge, the frequency response V(f) of the receiving amplifier should have a linear rise of 6 dB/octave up to approximately the frequency fo.

4 Claims, 12 Drawing Figures

ULTRASONIC TEST INSTRUMENT

BRIEF SUMMARY OF THE INVENTION

This invention relates to an ultrasonic test instrument for the nondestructive testing of materials comprising a transmitter, a receiving amplifier and wide-band test probes having different nominal frequencies used to generate and receive ultrasonic signals, and a variable attenuating resistor for adjusting the transmission pulse amplitude.

In order to obtain high spatial resolution when testing workpieces with ultrasonic instruments using standard test probes, very short ultrasonic frequency pulses must be used. For this purpose a transmission pulse of appropriate short duration energizes a highly attenuated ultrasonic test probe (wide-band test probe). The reflected echo signal is received by this wide-band test probe and the corresponding electrical signal is amplified in a wide-band amplifier. The electrical transmission pulse generally is produced by very rapidly discharging a capacitor which has been charged to a predetermined voltage. The discharge of the capacitor is effected by a circuit component acting as a switch (e.g. a transistor, a thyristor, etc.).

Depending upon the test problem, known ultrasonic instruments operate with test probes of different nominal frequencies. Hence, a pulse control is provided to match the transmitter to the test probe for causing the amplitude of the electrical transmission pulse to be adjustable. This pulse control is an attenuating resistor connected in parallel with the transmission output signal and, hence, also with the test probe and the receiver input. The pulse control is adjusted until the operator considers that the pulses shown on the instrument screen have an optimum appearance (maximum amplitude and distortion-free representation of the echo pulses).

Using this known method of matching the test probe to the transmitter, it has been found that different ultrasonic instruments require different adjustments. It is therefore most difficult to obtain a reproducible adjustment with this method. On the contrary, in some cases the adjustments are incorrect, thus resulting in erroneous signal evaluation, for it has been found that a change of resistance of the attenuating resistor results in a change of the frequency spectrum of the complete system comprising the transmitter, test probe and receiver. If, for example, a two MHz test probe is used, the highest sensitivity range may be at a frequency of one MHz in the event of an incorrect adjustment of the attenuating resistor.

An object of this invention is to provide an improved ultrasonic instrument which is designed so that a change of the pulse control has a minimum effect on the frequency spectrum of the complete instrument comprising the transmitter, the test probe and receiver.

To this end, according to the invention, the receiving amplifier has a frequency response V(f) adapted to whichever test probe is used, said frequency response being so selected that the product H(f) of the spectral distribution S(f) of the transmitter and the frequency response V(f) of the receiving amplifier is frequency-independent up to the nominal frequency fo of the particular test probe used and has its maximum value in this range. For all practical purposes it is sufficient for the product H(f) to be substantially constant between the frequencies fo and fo/10.

With the transmitters conventionally used in ultrasonic instruments and employing a capacitor discharge for pulse generation, the 1/f decrease of the corresponding transmission spectrum means that the frequency response of the receiving amplifier V(f) must satisfy the condition that V(f) has a linear rise of six dB/octave up to approximately the frequency fo.

Further details and advantages of the invention will be described hereinafter with reference to the drawings illustrating exemplified embodiments.

BRIEF DESCRIPTION OF THE DRAWINGS

Referring to FIG. 1, an ultrasonic transmitter 1 includes a thyristor 10, a capacitor 11 and a pulse control 12. The control electrode of thyristor 10 is connected to a trigger unit 3 via a conductor 2. The output of the transmitter 1 is connected via conductor 7 both to an ultrasonic test probe 4 and to the input of a wide-band receiving amplifier 5 which is coupled to an evaluating unit 6.

Figure 1:
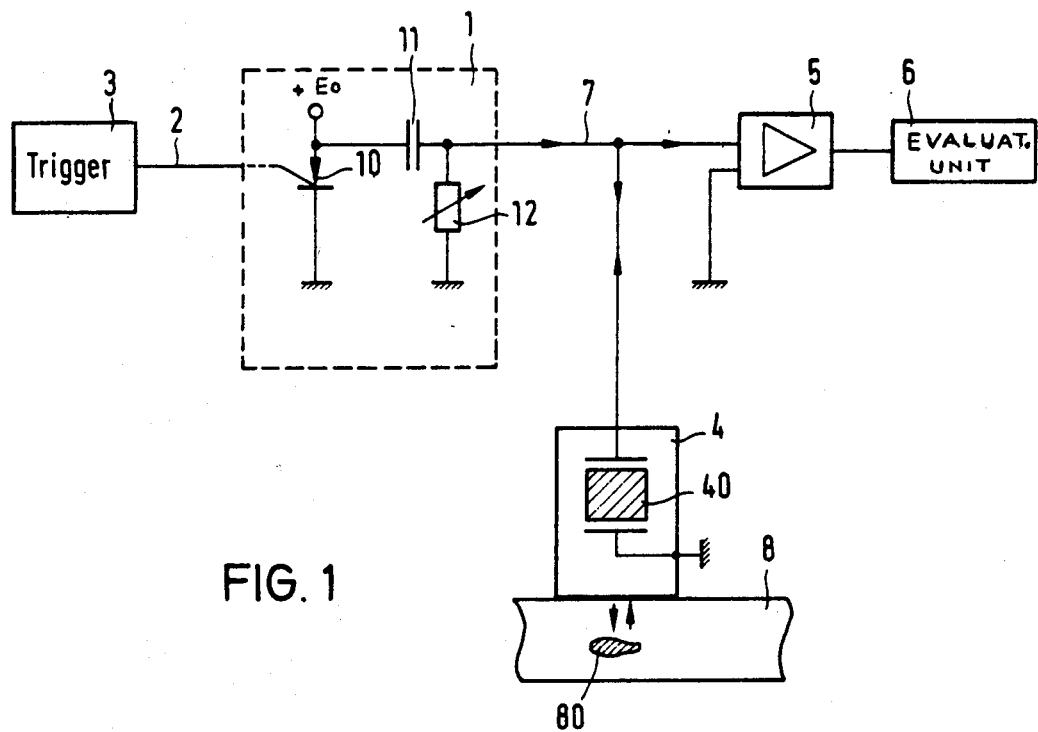
FIG. 1 is a schematic circuit diagram of a known ultrasonic test instrument with a pulse control.

The operation of such a circuit is known and will therefore be explained only to the extent that it appears necessary for an understanding of the present invention.

The trigger 3 generates pulses at predetermined time intervals, the pulses being fed via conductor 2 to the control electrode of the thyristor 10. The trigger pulse causes the thyristor 10 to become conductive so that the capacitor 11, previously charged with a voltage Eo, is discharged. A corresponding (discharge) pulse passes via conductor 7 to the piezoelectric element 40 of the test probe 4, which generates an ultrasonic pulse which enters the workpiece 8 under test, where the ultrasonic pulse is reflected at a defect 80. The echo signal returns to the piezoelectric element 40 and is converted into a corresponding electrical pulse which is then amplified in amplifier 5 and evaluated in the evaluating unit 6.

Figure 2:
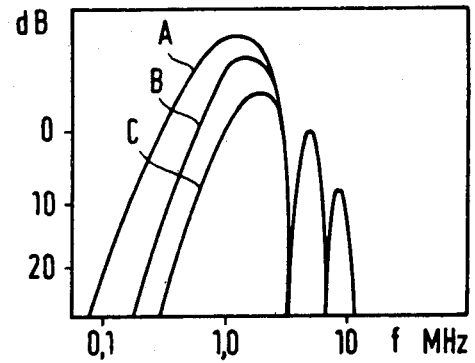
FIG. 2 is a diagram showing the spectral distribution of an ultrasonic instrument according to FIG. 1.

The amplitude of the transmitted pulse can be adjusted by means of the pulse control 12. As already stated, known ultrasonic instruments inadequately take into account the fact that a change of this pulse control results in a change of the frequency spectrum of the system comprising the transmitter 1, test probe 4 and amplifier 5. This may result in an incorrect evaluation of the defect, particularly when wide-band test probes are used. FIG. 2 shows the effects of the pulse control 12 on the overall frequency curve of the ultrasonic test system comprising the transmitter 1, test probe 4 and amplifier 5. The amplitude is plotted in decibels along the y-axis while the frequency is indicated in MHz along the x-axis. The center frequency of the test probe 4 is at 2 MHz. Curve A shows a frequency response with the resistance of the pulse control 12 equivalent to about 400 ohms. Curves B and C are plotted with resistance values of 100 and 50 ohms respectively. As will be seen from these curves, a change of the resistance of the pulse control 12 results both in a change of the amplitude of the pulse spectrum (sensitivity change) and a change of the start of the frequency spectrum. Finally, the center frequency of the main lobe at about 2 MHz also shifts, so that the maximum sensitivity is offset somewhat in relation to the center frequency of the test probe. The side lobes at 6 and 10 MHz are caused by the test probe 4 and are immaterial to the present invention.

Figure 3A:
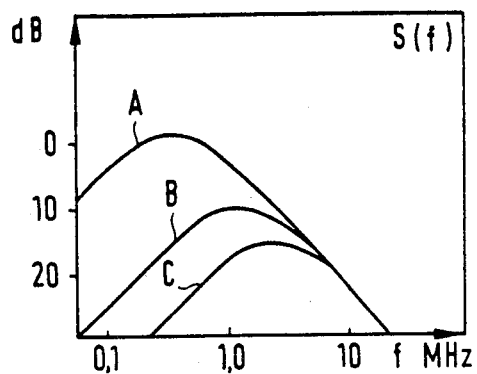
FIGS. 3a to 3d are diagrams showing the frequency responses and spectral distributions of transmitter S(f), of the receiving amplifier V(f), of the test probe P(f) and of the product H(f)=S(f)·V(f)

It has been found that the spectra illustrated in FIG. 2 for the complete system can be determined from the respective individual spectra for the transmitter 1, test probe 4 and amplifier 5. To this end, the product H(f) of the spectral distribution S(f) of the transmitter and the frequency response V(f) of the amplifier is formed, and then the product of H(f) and the frequency response of the test probe P(f) is determined. This is illustrated with reference to an example in FIGS. 3a to 3d:

FIG. 3a depicts the frequency spectrum of the transmitter 1 shown in FIG. 1. The frequency response of the transmitter is determined mainly by the 1/f decrease, which is determined by the thyristor acting as a switch. The capacitor 11 and the pulse control 12 act mainly as a high-pass filter. As in FIG. 2, a change in the resistance values of the pulse control results in a shift of the frequency spectrum.

Figure 3B:
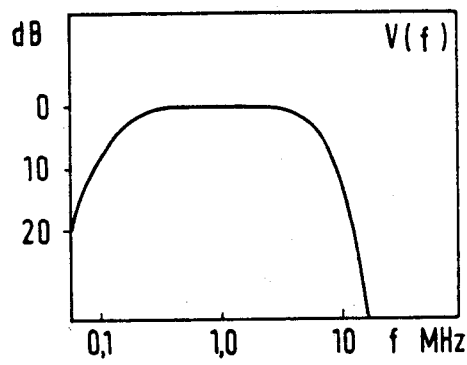

FIG. 3b shows the frequency response V(f) of the wide-band receiving amplifier 5.

Figure 3C:
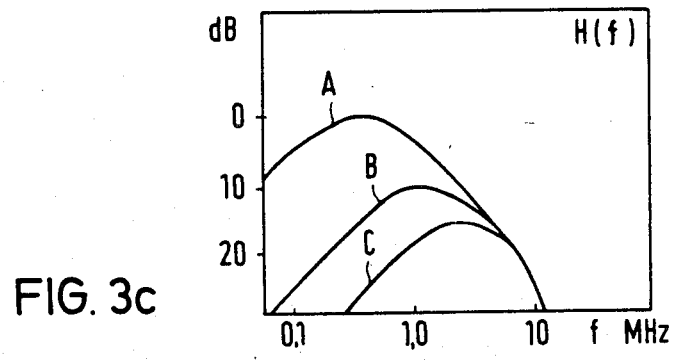
Figure 3D:
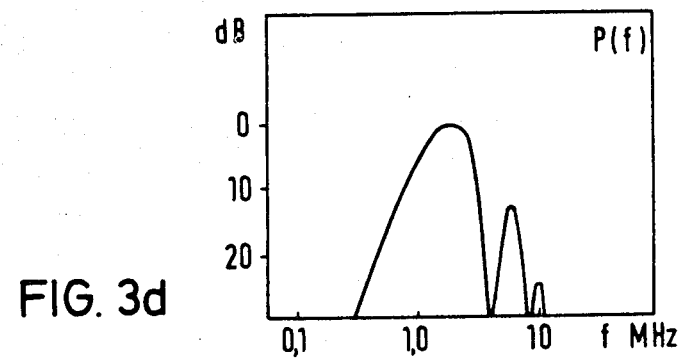

FIG. 3c shows the spectra H(f) of the product of the transmission spectrum S(f) and the frequency response of the amplifier V(f). It will be apparent that a change of the pulse control 12 results both in a frequency shift and a change of the maximum amplitude of the spectrum. This spectral change has a corresponding effect on the frequency spectrum of the 2 MHz test probe as shown in FIG. 3d and results in the composite frequency spectrum shown in FIG. 2.

In order to minimize the effect of the pulse control on the ultrasonic instrument frequency response, the present invention discloses the use of a narrow-band amplifier, adapted to whichever test probe 4 is used, instead of the wide-band amplifier 5. The frequency response of the narrow-band amplifier is so selected that the product H'(f) of the spectral response of the transmitter S'(f) and the frequency response of the receiving amplifier V'(f) is frequency-independent up the the nominal frequency fo of the test probe 4, and at least in the frequency interval between fo and fo/10.

Figure 4A:
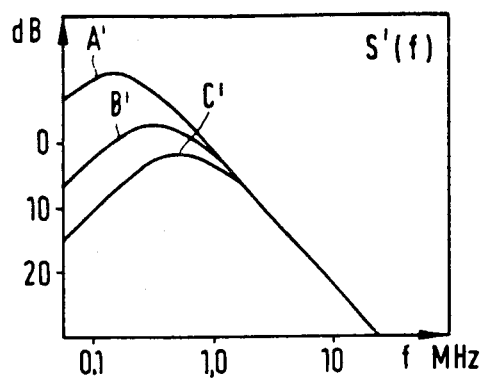
FIGS. 4a to 4d are diagrams showing the corresponding frequency responses to FIGS. 3a to 3c using an amplifier with a linear frequency rise up to the nominal frequency of the test probe, and the frequency response of the product H'(f) times P(f)

FIG. 4a shows a transmission spectrum S'(f) for three different resistance values of the pulse control 12. Curve A' corresponds to a 1,000 ohm resistance while curves B' and C' correspond to 400 ohm and 200 ohm resistances respectively.

Figure 4B:
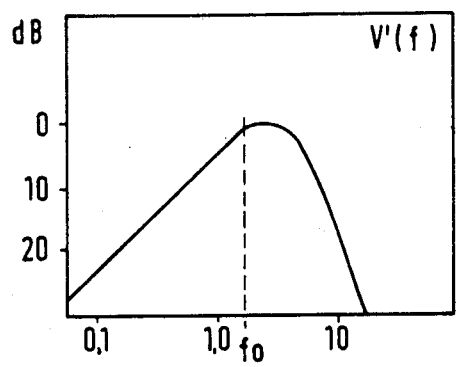

FIG. 4b shows the frequency response V'(f) of the receiving amplifier. The frequency response has a linear rise (6 dB/octave) approximately up to the nominal frequency fo (2 MHz) of the test probe. The 1/f sensitivity decrease of the transmitter (FIG. 4a) is thus compensated. The shape of the frequency response curve beyond fo is not critical and is determined by the frequency characteristic of the components following the amplifier.

Figure 4C:
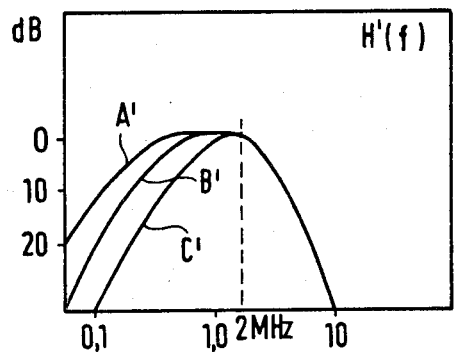
Figure 4D:
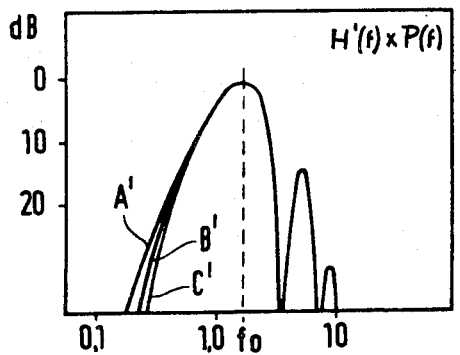

FIG. 4c shows the product H'(f) of S'(f) and V'(f); FIG. 4d shows the product of H'(f) and P(f), where P(f) denotes the frequency response of the test probe according to FIG. 3d.

As will be evident from FIG. 4d, unlike FIG. 2, a change of the pulse control 12 does not result in any change of the amplitude or any frequency-dependent shift of the center frequency. Only the start of the spectra is shifted slightly.

With regard to the purpose of the invention indicated hereinabove, it would be possible to delete the pulse control 12 completely, since optimum adjustment of the system comprising the transmitter, test probe and receiving amplifier is already obtained by selecting the amplifier frequency response in dependence on the nominal frequency of the test probe 4. However, it has been found, in practice, that the use of a pulse control is quite desirable. For very high values of the pulse control, or in the absence of this resistor (resistance value = ∞), the transmission pulses are much wider—due to damping processes—than in the case of smaller resistances, so that the effective range of the transmission pulse is also wider and, hence, the spatial resolution is reduced. For most applications it is sufficient for the pulse control to have a value of about 1,000 ohms. In that case, the resulting frequency spectrum (FIG. 4d) is still sufficiently wide and the transmission pulse range is sufficiently narrow. There are practical cases, however, where the transmission pulse range must be very narrow so that the resistance of the pulse control 12 is set to less than 1,000 ohm (e.g. 400 ohm), although in these cases the transmission range of the system comprising the transmitter 1, test probe 4 and receiving amplifier 5 is narrower than in the case of high resistance values.

Figure 5:
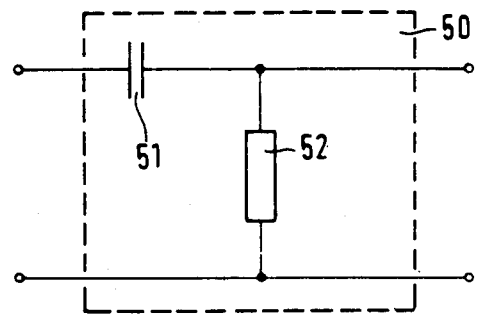
FIG. 5 is a schematic electrical circuit diagram of an RC filter for generating a frequency response as shown in FIG. 4b.

An amplifier having the frequency response shown in FIG. 4b can most easily be realized by the use of a wide-band amplifier connected to a high-pass filter as shown in FIG. 5. The high-pass filter consists basically of capacitor 51 and a resistor 52 (RC filter).

Figure 6:
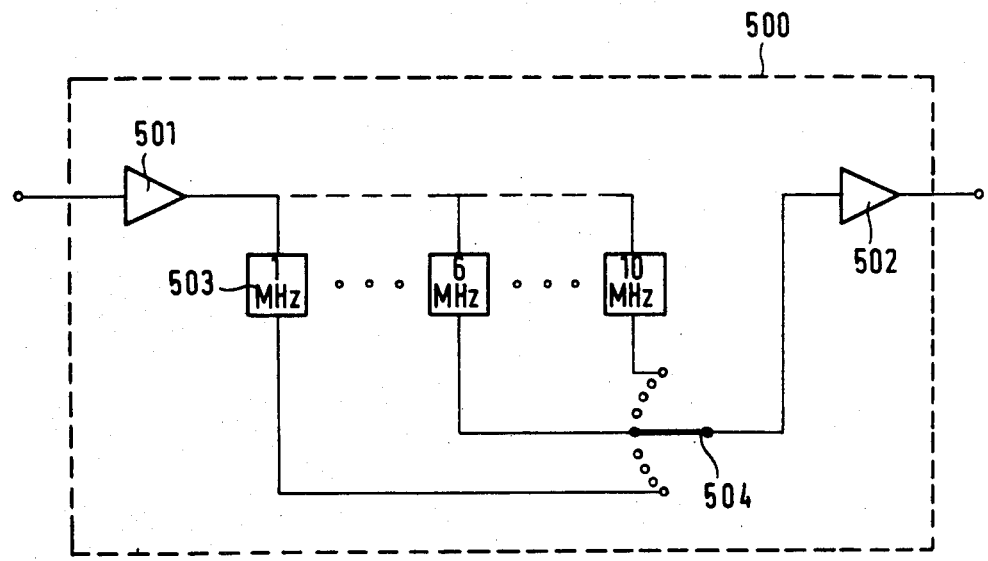
FIG. 6 is a schematic electrical diagram showing an amplifier arrangement for using ultrasonic wide-band test probes having different center frequencies fo.

If an ultrasonic instrument is to be used with more than one test probe with different center frequencies, it is advisable to replace the wide-band amplifier 5 in FIG. 1 by the amplifier 500 shown in FIG. 6. The amplifier 500 comprises basically two wide-band amplifier stages 501 and 502. High-pass filters 503 are disposed between these amplifiers, each filter corresponding to a test probe center frequency (e.g. from 1 to 10 MHz). The applicable filter corresponding to the center frequency of whichever test probe is used is then connected in circuit between the amplifiers 501 and 502 by a selector switch 504.

What is claimed is:

1. An ultrasonic test instrument comprising a transmitter, a receiving amplifier and wide-band test probes of different nominal frequencies fo, used for generating and receiving ultrasonic waves, and a variable attenuating resistor coupled for adjusting the transmission pulse amplitude, the improvement comprising:

the receiving amplifier having a frequency response V(f) matched to whichever test probe is used, the frequency response of said receiving amplifier being so selected that the product H(f) of the frequency spectrum response S(f) of the transmitter and the frequency response V(f) of the receiving amplifier is substantially constant approximately up to the nominal frequency fo of the test probe and at least in the range of the frequencies between fo and fo/10 and has a maximum value in that range.

2. An ultrasonic test instrument as set forth in claim 1, the maximum amplitude decrease of the frequency response V(f) of the receiver amplifier in the frequency range between fo and fo/10 is ≦Emax/10 for values of the attenuating resistor above one thousand ohm, Emax denoting the maximum amplitude of the product H(f).

3. An ultrasonic tester according to claim 1, or 2, the frequency response V(f) of the receiving amplifier having a linear rise of substantially 6 dB/octave up to approximately the frequency fo.

4. An ultrasonic test instrument as set forth in claim 1 or 2, the receiving amplifier comprising at least two wide-band amplifiers, a plurality of high-pass filters, each filter matched to the nominal frequency of a probe to be used, and switching means for selectively switching one of said filters serially in circuit between said amplifiers.

* * * * *